US009091675B2

(12) United States Patent
Couillard

(10) Patent No.: US 9,091,675 B2
(45) Date of Patent: Jul. 28, 2015

(54) CELLS AND CONNECTING CHANNELS FOR CENTRIFUGAL PARTITION CHROMATOGRAPHY DEVICES

(75) Inventor: Francois Couillard, Sene (FR)

(73) Assignees: IFP Energies Nouvelles, Rueil-Malmaison Cedex (FR); Francois Couilard, Sene (FR)

(*) Notice: Subject to any disclaimer, the term of this patent is extended or adjusted under 35 U.S.C. 154(b) by 847 days.

(21) Appl. No.: 12/677,033

(22) PCT Filed: Sep. 4, 2008

(86) PCT No.: PCT/FR2008/001230
§ 371 (c)(1),
(2), (4) Date: Mar. 8, 2010

(87) PCT Pub. No.: WO2009/066014
PCT Pub. Date: May 28, 2009

(65) Prior Publication Data
US 2010/0200488 A1 Aug. 12, 2010

(30) Foreign Application Priority Data

Sep. 6, 2007 (FR) .................................. 07 06258

(51) Int. Cl.
*G01N 30/42* (2006.01)
*B01D 15/18* (2006.01)

(52) U.S. Cl.
CPC ............ *G01N 30/42* (2013.01); *B01D 15/1892* (2013.01); *Y10T 29/49826* (2015.01)

(58) Field of Classification Search
CPC ............... G10N 30/42; B01D 15/1892; Y10T 29/49826
USPC ................................ 210/635, 656, 198.2, 657
See application file for complete search history.

(56) References Cited

U.S. PATENT DOCUMENTS 4,551,251 A * 11/1985 Kolobow et al. ............... 210/635
4,632,762 A * 12/1986 Ramsland ..................... 210/657
(Continued)

FOREIGN PATENT DOCUMENTS

FR 2 791 578 10/2000
FR 2 868 165 9/2005
(Continued)

OTHER PUBLICATIONS

L. Marchal et al.; Influence of flow pattern on chromatographic efficiency in centrifugal partition chromatography, Journal of Chromatography A., Feb. 2000, pp. 339-352, vol. 869, No. 1-2.
(Continued)

*Primary Examiner* — Ernest G Therkorn
(74) *Attorney, Agent, or Firm* — Fitch, Even, Tabin & Flannery LLP

(57) ABSTRACT

The present invention relates to cells (1) for a centrifugal partition chromatography column, consisting of stacked discs and comprising a network of three-dimensional cells interconnected in series and communicating with liquid phase circulation channels, said cells being distributed over the periphery of at least one disc driven into rotation about a main axis (8); the cells have a geometric shape of revolution about a substantially radial axis with respect to said disc and they are connected by channels (2, 4) of substantially circular, elliptical or parallelepipedic section, the main two dimensions of which are smaller than the largest cross-section of the cell.

The invention also relates to methods of manufacturing these cells.

13 Claims, 3 Drawing Sheets

(56) References Cited

U.S. PATENT DOCUMENTS

| | | | |
|---|---|---|---|
| 4,857,187 A | 8/1989 | Ito | |
| 4,877,523 A | 10/1989 | Nunogaki | |
| 4,968,428 A * | 11/1990 | Nunogaki | 210/635 |
| 5,935,430 A * | 8/1999 | Craig | 210/198.2 |
| 6,537,452 B1 * | 3/2003 | de La Poype et al. | 210/198.2 |
| 7,422,685 B2 * | 9/2008 | Couillard et al. | 210/198.2 |
| 2004/0173534 A1* | 9/2004 | Margraff et al. | 210/656 |
| 2006/0243665 A1* | 11/2006 | Couillard et al. | 210/635 |
| 2008/0035546 A1* | 2/2008 | Foucault et al. | 210/198.2 |

FOREIGN PATENT DOCUMENTS

| | | |
|---|---|---|
| FR | 2 852 104 | 9/2007 |
| JP | 2-67959 | 3/1990 |

OTHER PUBLICATIONS

L. Marchal et al.; Mass Transport and Flow Regimes in Centrifugal Partition Chromatography, AICHE Journal, Aug. 2002, pp. 1692-1704, vol. 48, No. 8.

* cited by examiner

US 9,091,675 B2

CELLS AND CONNECTING CHANNELS FOR CENTRIFUGAL PARTITION CHROMATOGRAPHY DEVICES

REFERENCE TO RELATED APPLICATIONS

This application is a 371 of PCT/FR08/01230 filed Sep. 4, 2008.

FIELD OF THE INVENTION

The present invention relates to the sphere of centrifugal liquid-liquid chromatography devices, and more particularly to cells and their connecting channels for centrifugal liquid-liquid chromatography devices, and to the method of manufacturing same.

BACKGROUND OF THE INVENTION

A known technique for separating constituents A and B in solution in a liquid mixture consists in injecting the latter into a chromatography column subjected to a centrifugal force, intended to allow one of the liquid phases to be percolated in the other liquid phase and vice versa (CCC or CPC chromatography).

In practice, as shown notably in patents FR-2,791,578, U.S. Pat. No. 4,877,523 or U.S. Pat. No. 4,857,187, this type of chromatography system comprises one or more stacks of discs driven into rotation. Each one comprises in the thickness thereof and over the entire periphery thereof a succession of cells arranged in a radial or oblique direction and connected in series by a set of circuits of fine winding channels at the ends of each cell. The circuits of all the discs communicate with one another. The cells and their communication circuits are filled with a stationary liquid phase kept in place by the centrifugal force and another mobile liquid phase that percolates the stationary phase.

Rotation of the stack creates a high centrifugal acceleration field that allows to keep in place the liquid phase referred to as fixed stationary phase, whereas the mobile phase circulates in ascending mode if it is lighter than the stationary phase, and in descending mode if it is heavier.

Separation of the constituents of a feed in liquid solution consisting of at least two constituents having different partition coefficients, such that they are entrained at unequal velocities by the mobile phase that can be one or the other of the liquid phases, is carried out in this type of device consisting of the interconnection in series of one or more chains of cells.

The chromatographic process, i.e. partition of the molecules to be purified between the two liquid phases, takes place in each cell, and mass transfer is favoured by a good dispersion of the mobile phase coming from the channel in each cell.

A first and double drawback of this prior art is due to the design of the cells driven through the thickness of the discs, which requires seals, generally flexible, made of Teflon par example, between each disc, thus closing each cell along the plane of the disc, therefore perpendicular to the main axis of each cell. Even if the cell has rounded shapes to facilitate dispersion homogeneity for a better matter exchange between the two phases, the bond lines create with the cell right angles that are not favourable to homogeneous dispersion of the liquids. Finally, these flexible bond lines subjected to continuous liquid pressure variations deform over time and they modify the geometry of the cells, hence aging of the device.

A second drawback lies in that the cells are connected to each other by a ribbon-shaped channel. It can be readily calculated and checked that this line shape, for a given section, produces a pressure drop that is much higher than that caused by a line of same section, but square or cylindrical. In order to limit too high pressures and, in some cases, for machining difficulty reasons, the thickness of these lines has to be increased, thus increasing the dead volumes in which the products being separated partly mix again, which reduces the efficiency and the productivity of the device. Furthermore, if the thickness of the line is not perfectly constant over the entire length thereof, which is the case when the cells are water jet cut, a gradient of the velocity vectors of the mobile liquids (phase and compounds to be separated) appears between one face of the disc and the other, which tends to spread the compounds that are being separated, therefore to remix them and consequently to reduce the efficiency and productivity performances of the machine.

SUMMARY OF THE INVENTION

The object of the present invention thus is to overcome one or more drawbacks of the prior art by providing cells (1) for a centrifugal partition chromatography column, consisting of stacked discs and comprising a network of three-dimensional cells interconnected in series and communicating with liquid phase circulation channels, distributed over the periphery of at least one disc driven into rotation about a main axis (8), the cells having a geometric shape of revolution about a substantially radial axis with respect to said disc and being connected by channels (2, 4) of substantially circular, elliptical or parallelepipedic section, the two main dimensions of which are smaller than the largest cross-section of the cell.

In an embodiment of the invention, the geometric shape of revolution is defined by three main dimensions along three axes X-X', Y-Y' and Z-Z', Z-Z' being parallel to the axis of rotation of the disc, axis Y-Y' being radial with respect to the disc and axis X-X' orthogonal to the other two axes, said three dimensions being substantially identical.

In another embodiment of the invention, the dimension along axis X-X' is greater than the other two dimensions along axes Z-Z' and Y-Y'.

In another embodiment of the invention, the dimension along axis Y-Y' is greater than the other two dimensions along axes Z-Z' and X-X'.

In another embodiment of the invention, the dimension along axis Z-Z' is greater than the other two dimensions along axes Y-Y and X-X'.

In another embodiment of the invention, the dimensions along axes X-X', Y-Y' and Z-Z' are different.

The cells according to the invention can be laid out at least two by two, one after the other, along axis Y-Y', forming at least one pair (5) of cells regularly repeated on a circle parallel to the plane of rotation of disc (3).

In an embodiment of the invention, cells (1) are laid out in at least two concentric circles parallel to the plane of rotation of disc (3).

Cells (1) of pair of cells (5) according to the invention are connected by an S-shaped liquid phase circulation channel (4).

In an embodiment of the invention, the axis made up of the inlet of the liquid phase circulation channels is parallel to axis Y-Y'.

In another embodiment of the invention, the axis made up of the inlet of the liquid phase circulation channels is superposed on axis Y-Y'.

In another embodiment of the invention, the axis made up of the inlet of the liquid phase circulation channels is offset with respect to axis Y-Y'.

The invention also relates to a method of manufacturing cells (1) according to the invention, consisting in machining half-cells on a disc (3) and its mirror (3'), discs (3, 3') being then assembled two by two so as to form an entire cell (1).

In an embodiment of the invention, discs (3, 3') are assembled by welding.

In another embodiment of the invention, they are assembled by a joint (6).

In another embodiment of the invention, liquid phase circulation channels (7) are directly formed within the joint.

As described more in detail hereafter, these new cell and channel forms are likely to increase the efficiency and the productivity of chromatography devices.

BRIEF DESCRIPTION OF THE FIGURES

Other features and advantages of the invention will be clear from reading the description hereafter of embodiments, given by way of non limitative examples, with reference to the accompanying figures wherein.

DETAILED DESCRIPTION

Figure 1:
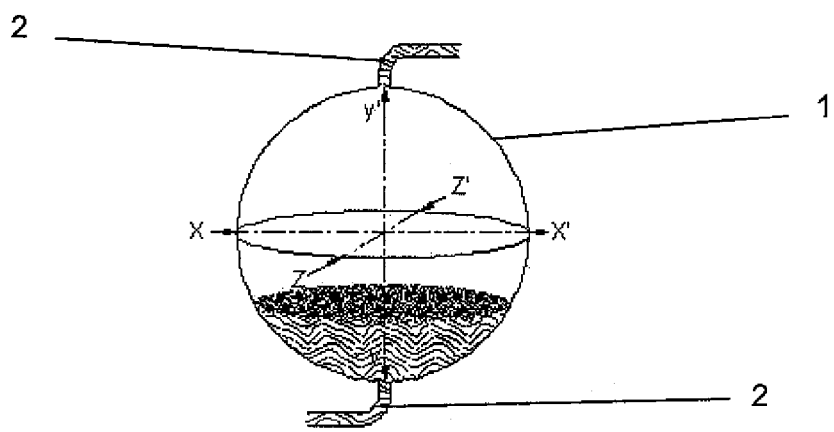
FIG. 1 is a flow sheet of a cell according to the invention, with inlet and outlet channels of substantially round, square or rectangular section according to the invention.

FIG. 1 illustrates a cell (1) according to the invention. The base of this cell (1) has a revolution geometry. The shape of the cells according to the invention can thus range from spheres to spheroids to other similar revolution shapes by modifying the respective length ratios of axes X-X', Y-Y' and Z-Z'. Axis Z-Z' being parallel to the main axis of rotation (8) of the disc comprising the cells illustrated in FIG. 8, axis Y-Y' being radial with respect to the disc and axis X-X' orthogonal to the other two axes (FIGS. 1, 2, 3, 4, 5, 6 and 7).

Such a shape, compared with the cells with angular parts of the prior art, favours better dispersion of the mobile phase in the stationary phase and, consequently, allows better matter exchange, which leads to improved separation. The axis of revolution of the shape of the cells is close to the radial direction of the discs. Preferably, the axis of revolution is in the radial direction.

Figure 9:
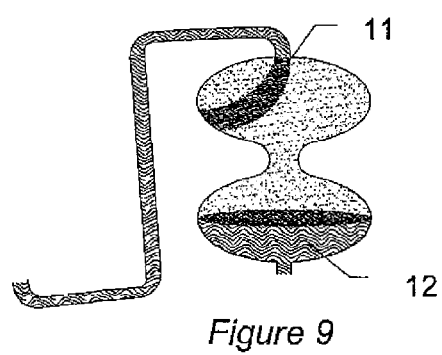
FIG. 9 shows the distribution of the liquids in cells according to the invention.

Channels (2, 4) connecting these cells have a section defined by two main directions that determine the shape thereof. Thus, depending on the length of the axes defined by the two main directions, the cells have a circular, square or rectangular section, or a section very close to one of these shapes, the section of the channels being smaller than the largest cross-section of the cell. The cross-section of the cell is defined as the section perpendicular to the radial axis with respect to the disc. This section of the cells can also be defined by axes X-X' and Z-Z'. This type of channel shape allows to decrease the pressure drop due to the liquid stream and also to decrease the dead volume while improving the profile of the velocity vectors of the liquids in relation to a ribbon-shaped line. More generally, these channels can have a section whose two main directions are smaller than the dimensions along axes X-X' and Z-Z' of the cell. For example, the width and the length of a rectangle section are smaller than the dimensions along axes X-X' and Z-Z' of the cell. The same applies to a polygonal section with its main diagonals. These lines (2, 4) are connected in the axis Y-Y' shown in FIG. 1 or slightly off-centre. In fact, experimentation shows that the Coriolis force associated with an offset of the inlet axis of the mobile phase in the cell considerably improves the dispersion homogeneity of spray (11) illustrated in FIG. 9 in cell (1).

In order to adjust the shape of these cells (1) to the various groups of two-phase systems and to the various chromatography device sizes, the respective dimensions are optimized along axes X, Y and Z. The shapes of revolution are thus modified along the 3 axes of the cell. Axis Y is substantially on the same axis as that of the centrifugal force. It is well known that the hydrostatic pressure, for a given force, increases with the height of the cell along this axis. In case of upscaling such a device, upscaling is limited along axis Y and upscaling the dimensions of the cell along axes X and Z is favoured in order to limit this pressure.

Figure 2:
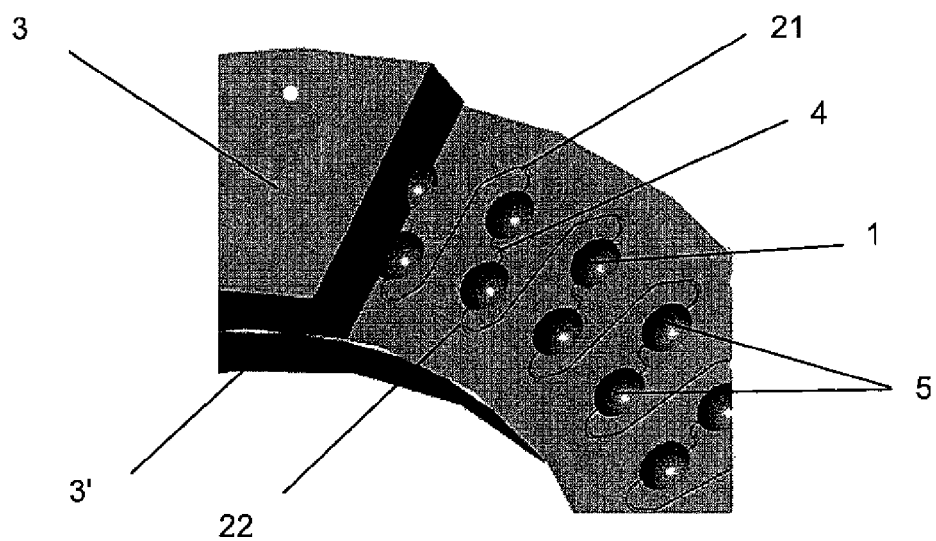
FIGS. 2, 3 and 4 show various embodiments of the cells and channels according to the invention.
Figure 3:
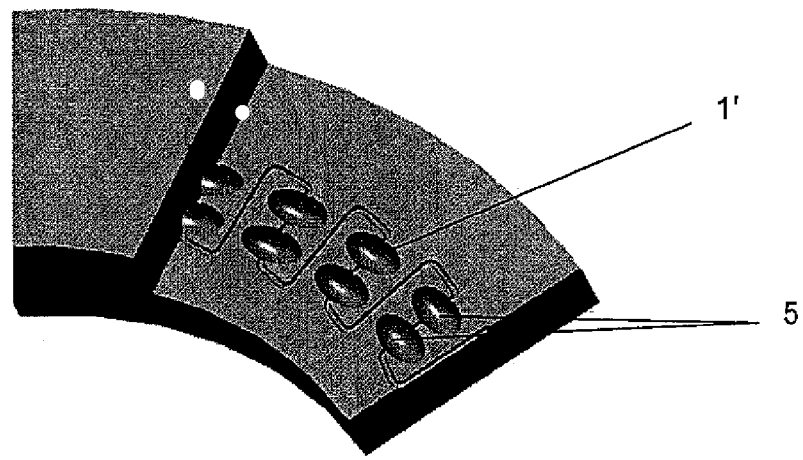
Figure 4:
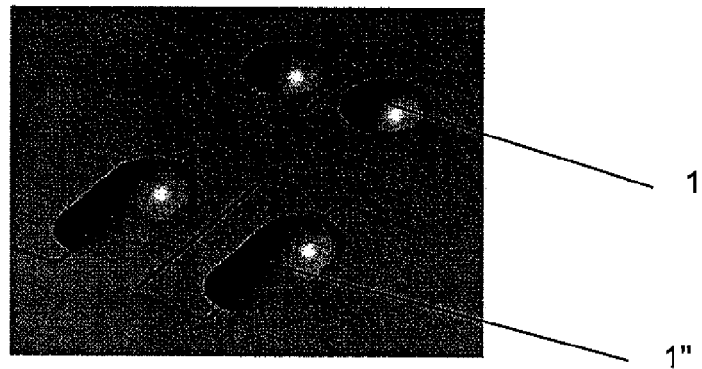
Figure 5:
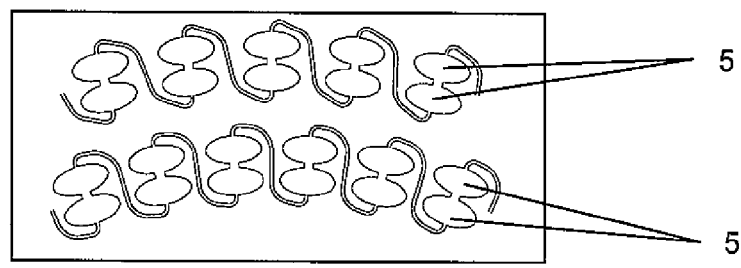
FIG. 5 shows an example of concentric assemblies of cells on a single disc allowing the useful capacity of a rotor to be increased.

FIGS. 2, 3 and 4 illustrate various cell shapes obtained by modifying the dimensions according to axes X, Y and Z.

In FIG. 2, cells (1) are spherical, the dimensions along axes X, Y and Z have substantially the same values. In FIG. 3, cells (1') are ovoid, it is the dimension along axis X that has been increased in relation to that of axes Y and Z. FIG. 4 illustrates two cell types, spherical (1) and ovoid (1"), whose dimensions along axis Y have been increased, arranged on two concentric circles. More generally, it is thus possible to have cells whose dimensions along the three axes X-X', Y-Y' and Z-Z' are all identical, all different, or two dimensions of which are equal.

FIGS. 2, 3, 5, 6 and 7 show an example of another embodiment of the invention, the "Twin" or pair mode (5), where the cells are grouped two by two in series and connected to one another by channels (4). These figures are not limitative because, in some applications, it is interesting to have groups of several cells based on the "Twin" mode principle. For example, in the case of FIG. 5, the cell pairs (5) are arranged on two concentric circles. These configurations representing the pair version are given by way of non-limitative example because the same systems can be achieved with one or more cells.

With this type of device with single, double or more cells, the best performances are obtained when the mobile phase enters the stationary phase at a high velocity, which triggers a spray that increases the exchange surface between the two phases. In ascending mode, the centrifugal force causes the heavy stationary phase to be pressed in angled inlet line (21). In ascending mode, the light mobile phase has to pass between the wall of the line and this stationary phase, which reduces the section of flow. The light phase thus gathers speed and triggers the spray. The same applies to the descending mode in bend (22). This is not the case at a low flow rate with channel (4) because it is on the axis of the force and, in some cases, spray (11) is not triggered in the second cell of the pair. In some applications, it is interesting to connect the cells in pairs by an S-shaped channel (4), illustrated in FIG. 2, or any other shape close to an S, in order to produce spray (11) in the second cell.

In other applications, with viscous phases of very close densities for which separation is difficult (because of a low coalescence) (12), it is necessary to enlarge channel (4)

between the two pair cells in order to prevent spray (11) in the second pair cell so as to reduce the turbulences hindering coalescence.

These cells can be achieved in different ways.

Figure 6:
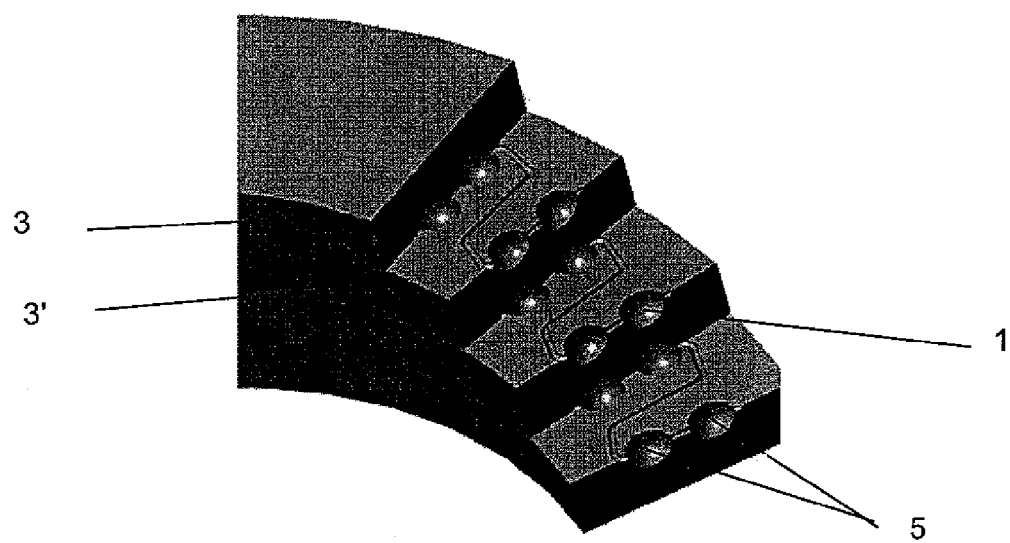
FIGS. 6, 7 and 8 show disc construction and assembly examples.
Figure 8:
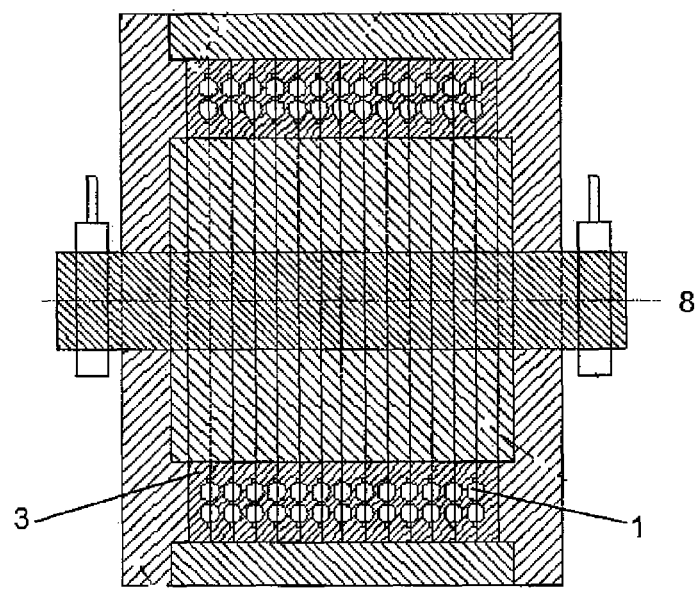

A first manufacturing process consists in machining half-cells on a disc (3) and its mirror (3') or symmetrical to the flank of the disk, as illustrated for example in FIG. 6 showing cross-sectional views of a stack of four discs according to the invention. In this case, the end discs are machined on a single face only, whereas the other discs are machined on both faces. The discs are then assembled so as to form entire cells through electronic beam welding or any other molecular-scale surface welding process. The discs can be made of plastic such as Teflon and pressed against one another, thus providing directly sealing (FIG. 8).

Figure 7:
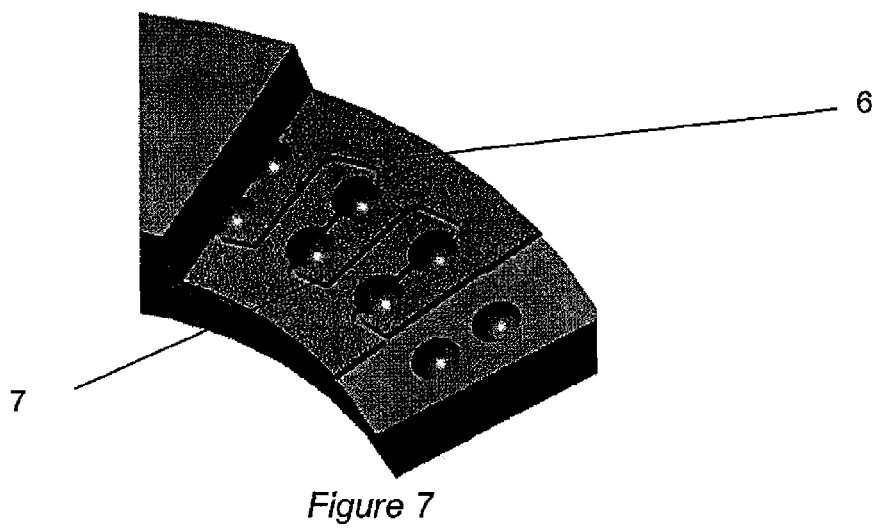

Another way of assembling the discs consists in arranging a joint (6) cut along the contour of the cells. In this case, it is possible to use the joint in the thickness thereof to achieve channels (7) as illustrated in FIG. 7. This joint (6) can be made of plastic and packed between discs (3, 3'), or made of metal and fastened as explained above, by means of a known surface welding method. Thus, the discs must be machined only to achieve the half-cell shapes, without machining the half channels.

Another manufacturing method consists in making the cells by lost wax casting, a method that is well known for example in the aeronautics industry where it is used for manufacturing turbine blades for reactors.

The cells can also be manufactured through plastic injection/extrusion, a method that is well known to the person skilled in the art.

It is clear to the person skilled in the art that the present invention should not be limited to the above details and that it allows embodiments in many other specific forms without departing from the field of application of the invention.

The present embodiments should therefore be considered by way of illustration, they can be modified without however departing from the scope defined by the accompanying claims.

The invention claimed is:

1. Cells for a centrifugal partition chromatography column including stacked discs, comprising:

a network of three-dimensional cells, wherein the cells are distributed over a periphery of at least one disc driven into rotation about a main axis, the cells have a spherical, spheroid, or ovoid geometric shape of revolution defined by three main dimensions along three axes X-X', Y-Y' and Z-Z', the axis Z-Z' being parallel to the axis of rotation of the disc, the axis Y-Y' being radial with respect to the disc, the axis X-X' being orthogonal to the other two axes, and a cross-section of a cell being perpendicular to the axis Y-Y' across the axis X-X' and the axis Z-Z', wherein each of the cells is formed from a first half cell formed on a first disc and mated with a second half cell formed on a second disc, the first half cell having a structure mirroring the second half cell, and wherein the cells are grouped two by two in series forming pairs of cells; and liquid phase circulation channels interconnected to, and communicating with, the cells in series, wherein the channels have a substantially circular, elliptical or parallelepipedic section, and the main two dimensions of the section of the channels are smaller than the largest dimensions of the cross-section of the cell, wherein the two cells of each pair of cells are connected to one another by an S-shaped liquid phase circulation channel, and each pair of cells connected with another pair of cells by another S-shaped liquid phase circulation channel.

2. Cells as claimed in claim 1, whose three dimensions along the three axes X-X', Y-Y' and Z-Z' are substantially identical.

3. Cells as claimed in claim 1, whose dimension along axis X-X' is greater than the other two dimensions along axes Z-Z' and Y-Y'.

4. Cells as claimed in claim 1, whose dimension along axis Y-Y' is greater than the other two dimensions along axes Z-Z' and X-X'.

5. Cells as claimed in claim 1, whose dimension along axis Z-Z' is greater than the other two dimensions along axes Y-Y' and X-X'.

6. Cells as claimed in claim 1, whose dimensions along axes X-X', Y-Y' and Z-Z' are different.

7. Cells as claimed in claim 1, characterized in that the cells of each pair of cells are laid out one after the other along axis Y-Y', and are regularly repeated on a circle parallel to the plane of rotation of disc.

8. Cells as claimed in claim 1, characterized in that the cells are laid out in at least two concentric circles parallel to the plane of rotation of disc.

9. Cells as claimed in claim 1, characterized in that the axis made up of the inlet of the liquid phase circulation channels is parallel to axis Y-Y'.

10. Cells as claimed in claim 9, characterized in that the axis made up of the inlet of the liquid phase circulation channels is superposed on axis Y-Y'.

11. Cells as claimed in claim 9, characterized in that the axis made up of the inlet of the liquid phase circulation channels is offset with respect to axis Y-Y'.

12. Cells as claimed in claim 1, wherein the first disc and the second disc are stacked and included in the stacked discs.

13. Cells as claimed in claim 1, wherein the first disc and the second disc are stacked two by two in the stacked discs.

* * * * *